United States Patent
Nagai et al.

(10) Patent No.: US 7,250,491 B2
(45) Date of Patent: Jul. 31, 2007

(54) HEMOLYTIC ACTIVE PROTEINS AND GENES ENCODING THE SAME

(75) Inventors: Hiroshi Nagai, Osaka (JP); Terumi Nakajima, Tokyo (JP)

(73) Assignee: Suntory Limited, Osaka-shi (JP)

( * ) Notice: Subject to any disclaimer, the term of this patent is extended or adjusted under 35 U.S.C. 154(b) by 358 days.

(21) Appl. No.: 10/651,250

(22) Filed: Aug. 29, 2003

(65) Prior Publication Data

US 2005/0074864 A1    Apr. 7, 2005

Related U.S. Application Data

(62) Division of application No. 09/647,522, filed on Dec. 1, 2000, now Pat. No. 6,653,449.

(30) Foreign Application Priority Data

Apr. 1, 1998   (JP) .................. 10-088569

(51) Int. Cl.
*C07K 16/00* (2006.01)
*A61K 39/395* (2006.01)

(52) U.S. Cl. .................. 530/387.1; 530/387.9; 424/130.1; 424/139.1

(58) Field of Classification Search .................. None
See application file for complete search history.

(56) References Cited

OTHER PUBLICATIONS

Nagai et al. Biosci. Biotechnol. Biochem. 2002. 66(1):97-102.*
Lederman et al. Molecular Immunology 1991, 28: 1171-1181.*
Li et al. PNAS 1980. 77: 3211-3214.*
G. Rottini, et al., "Purification and Properties of a Cytolytic Toxin in Venom of the Jellyfish *Carybdea marsupialis*" Toxicon, vol. 33, No. 3, Mar. 1995, pp. 315-326.
L. Cariello, et al., "Isolation and partial characterization of rhizolysin, a high molecular weight protein with hemolytic activity, from the jellyfish *Rhizostoma pulmo*" Toxicon, vol. 26, No. 11, 1988, pp. 1057-1065.
M. Tamkun, et al., "Isolation and partial characterization of a hemolytic and toxic protein from the nematocyst venom of the Portuguese Man-of-War, *Physalia physalis*" Biochemistry and Biophysical Acta, vol. 667, No. 1, 1981, pp. 87-98.
H. Azuma, et al., "Platelet aggregation caused by a partially purified jellyfish toxin from *Carybdea rastonii*" Toxicon, vol. 24, No. 5, 1986, pp. 489-899.
H. Nagai, et al., "Novel proteinaceous toxins from the box jellyfish (Sea Warp) *Carybdea rastoni*" Biochemical and Biophysical Research Communications, vol. 275, No. 2, Aug. 28, 2000, pp. 582-588.
Allison, et al., "Cloning and Characterization of a Prevotella Melaninogenica Hemolysin" Infect. Immun., vol. 65, No. 7, Jul. 1997, pp. 2765-2771.
Sato, A., "Toxins of *Carybdea rastonii*" Ochanomizu Igaku Zasshi, 1985, vol. 33, No. 2, pp. 131-151. (abstract) Toxcenter [Bioscience on STN] Retrieved from: STN International, Columbus, OH, USA. Accession No. CA10321175714H.
Tamken, et al., "Isolation and Partial Characterization of a Hemolytic and Toxic Protein from the Nematocyst Venom of the Portuguese Man-of-War" *Physalia physalis*. 1981, Biochim. Biophys. Act, vol. 667, pp. 87-98.
Smith, et al., "The Challenges of Genome Sequence Annotation or 'The devil is in the details'" 1997, Nature Biotechnol. vol. 15, pp. 1222-1223.
Doerks, et al., "Protein Annotation: Detective Work for Function Predication" 1998, Trends in Genetics, vol. 14, No. 6, pp. 248-250.
Nagai, et al., "Novel Proteinaceous Toxins from the Box Jellyfish (Sea Wasp) *Carybdea Rastonii*" 2000, Biochem. Biophys. Res. Comm., vol. 275, pp. 582-588.
Zhang, et al., "Environment-Dependent residue contact energies for proteins" Mar. 2000, Proc. Natl. Acad. Sci., vol. 97, No. 6, pp. 2550-2555.

* cited by examiner

*Primary Examiner*—Phillip Gambel
*Assistant Examiner*—Chun Crowder
(74) *Attorney, Agent, or Firm*—Crowell & Moring LLP

(57) ABSTRACT

Novel proteins providing the new approach to development of the drugs and pesticides with the use or application of a hemolytic activity, and novel proteins having the following properties and the genes encoding thereof are provided:

(1) having hemolytic activity;
(2) having a molecular weight of about 50,000 Da (determined by SDS gel electrophoresis);
(3) having an amino acid sequence represented by any of SEQ ID NO 1 to SEQ ID NO 3 as a partial amino acid sequence; and
(4) having an amino acid sequence represented by SEQ ID NO 5 as the full amino acid sequence.

2 Claims, No Drawings

HEMOLYTIC ACTIVE PROTEINS AND GENES ENCODING THE SAME

CROSS-REFERENCE TO RELATED APPLICATIONS

This application is a division of U.S. patent application Ser. No. 09/647,522 filed Dec. 1, 2000, now U.S. Pat. No. 6,653,449, which is a 371(c) National Stage of PCT/JP99/01607 filed Mar. 30, 1999, which claims priority to Japanese patent application Serial No. JP10-088569 filed Apr. 1, 1998, the disclosures of which are hereby incorporated in their entirety.

BACKGROUND OF THE INVENTION

1. Technical Field

The present invention relates to proteins having a hemolytic activity and genes encoding them. More specifically, the present invention relates to novel proteins having the hemolytic activity, a process for producing and the use of the same as well as antibodies for such proteins.

2. Background

The sting injury by the jellyfish in sea bathing has occurred in various parts of the world. The sting injury by *Carybdea rastonii* or *Physalia physalis* has also occurred frequently in Japan every year in the season of sea bathing of the summertime. The degree of the symptom by sting differs by species of a jellyfish and the individual differences of patients. The first symptom is dermotoses, such as pain, flare, papule, vesicle and so on in the sting site. In a serious illness, patients may die with generating of hemorrhagic maculae and the necrosis, and also constitutional symptom, such as headache, high fever, nausea, dyspnea, and the fluctuation of a pulse. Although such sting injury is occurring frequently, the determination and pharmacological properties of the toxic components of jellyfish have not been studied intensively. Therefore, the development of medicines for treatment of the sting by the jellyfish is also hardly performed before the present invention.

The studies on the toxic components of *Carybdea rastonii* have reported by Sato et al., and they found that there are some active substances having physiological activities, such as hemolysis, platelet agglutination, mast cell degranulation, the vessel smoothness muscle contraction, the dermal necrosis, the heart poison and the fatality in the crude extract fractions from the freeze-dried tentacle of *Carybdea rastonii*. They also examined on the platelet agglutination effect and vessel smoothness muscle contraction effect of the toxic component (Akihiko Sato, "Research on the toxic component of *Carybdea rastonii*", The Journal of the Ochanomizu Medico-dental Society, vol. 33, No. 2, 131-151, June, 1985).

On the one hand, since the poison from the nematocyst of a jellyfish was a non-dialyzable high polymer and deactivated by treatment with acid or alkali, or by heating processing, organic solvent processing, protease processing, etc., it was thought that the main components of this poison were proteins.

Moreover, the purification of the protein toxin derived from a jellyfish has also been tried; however, the isolation and the purification of the active components maintaining the hemolytic activity were not performed since the toxin of a jellyfish itself was very easy to be deactivated. Therefore, the physical and chemical properties of the toxin from jellyfish were not known up to now.

The detailed studies on the toxic component of a jellyfish is very important for the development of drugs applying their various physiological activities, in particular, specific hemolytic activity and the platelet agglutination effect.

Therefore, the problems to be solved by the present invention is providing an approach to development of the drugs for treatment of the sting injury by the jellyfish by means of isolating the proteins or peptides having as potent hemolytic activity as possible, in the state where the physiologic activity is retained. The present invention further provides the approach to study similarities on embryology or structure, and the species specificity of the protein having hemolytic activity to evaluate the structure-activity relationship thereof.

SUMMARY OF THE INVENTION

The inventors extensively performed the research for isolating the proteins having the hemolytic activity from the nematocyst of Carybdea rastonii using the hemolytic activity as the parameter, while retaining these hemolytic activities. As the result, they found out the process for isolating and purifying the proteins retaining hemolytic activities, and found that the protein from *Carybdea rastonii* had the partial chemical structure consisting the following amino acid sequences (1)-(3), and the molecular weight of about 50,000 Da (determined by SDS gel electrophoresis).

Amino acid sequence (1):

Gly-Glu-Ile-Gln-Thr-Lys-Pro-Asp-Arg- (SEQ ID NO: 1)

Val-Gly-Gln-Ala-Thr

Amino acid sequence (2):

Gly-Asn-Ala-Glu-His-Val-Ala-Ser-Ala- (SEQ ID NO: 2)

Val-Glu-Asn-Ala-Asn-Arg-Val-Asn-Lys

Amino acid sequence (3):

Met-Ser-Asp-Gly-Phe-Tyr-Thr-Met-Glu- (SEQ ID NO: 3)

Asn-Ser-Asp-Arg-Arg-Lys (wherein, an amino acid residue is written by the 3 letters notation defined by IUPAC and IUB)

Furthermore, they prepared the primers based on their partial chemical structures of the protein, and analyzed the gene sequence of about 1,000 base pair of said protein by conducting the RT-PCR on the total RNA prepared from the tentacle of Carybdea rastonii by using these primers. Consequently, they further determined the full primary amino acid sequence of the hemolytic active protein of *Carybdea rastonii* by means of analyzing the gene sequence at the 5'-end and 3'-end using the 5' RACE method and 3' RACE method.

Therefore, one embodiment of the present invention provides the specific protein having the amino acid sequence represented by (SEQ ID NO:5), or the amino acid sequence modified by the addition and deletion of one or more amino acid, and/or the substitution by other amino acid to said amino acid sequence, with the above-mentioned physiological, physical and chemical properties.

Another embodiment of the present invention also provides the process for preparing such proteins.

Furthermore, another embodiment provides the gene encoding such proteins, the process for preparing the specific proteins using the gene, and the drugs or the pesticides using the same.

The present invention further provides the pharmaceutical compositions or the pesticides containing the proteins using these properties, particularly, the pharmaceutical compositions having the platelet agglutination effect etc.

Moreover, since a specific antibody can also be obtained from this hemolytic active protein according to a conventional method (Cell Technology, separate volume, "Experimental protocol of antipeptide antibody", Shujunsha Co.), the present invention also provides the pharmaceutical compositions containing said antibody.

The isolation and purification of the proteins having the specific physiological activity provided by the present invention can specifically be performed as follows. For example, the ultrasonication of the nematocyst of *Carybdea rastonii* is carried out in phosphoric acid buffer solution, and then supernatants are collected by the centrifugal separation to obtain a crude extract. The object proteins can be separated and purified by subjecting this crude extract to ion exchange high performance liquid chromatography using TSK-GEL™ (Toso Co.), and the gel filtration high performance liquid chromatography with Superdex-75™ (Pharmacia Co.).

The structure of the protein provided according to the present invention obtained in this way can be determined by combining the analysis procedure of the amino acid sequence by the selective degradation using the enzyme, and the analysis procedure of a gene sequence using the PCR method etc. For example, the amino acid sequence can be determined by processing the protein separated and purified as mentioned above with a lysylendopeptidase, fractionating the fragment using a high performance liquid chromatography, and analyzing it using an amino acid sequencer etc. Next, the gene sequence of the proteins can be determined by RT-PCR method etc. using the primers prepared on the basis of the amino acid sequence. Finally, the full primary amino acid sequence of the proteins can be clarified by determining the amino acid sequence on the basis of the gene sequence.

It was confirmed by such analysis that the protein provided according to the present invention has the molecular weight of about 50,000 Da (measured by SDS gel electrophoresis), and the partial amino acid sequences have the above-mentioned amino acid sequences (1) to (3).

As a result of a homology search on the partial amino acid sequences, the homology between the protein of the present invention and the known proteins was very low. Therefore, it was suggested that the protein of the present invention having the hemolytic activity is completely novel protein, which is not similar to the known proteins.

Next, the determination of the gene sequence of about 1,000 base pairs by performing RT-PCR to total RNA prepared from the tentacle of *Carybdea rastonii* using the primers prepared on the basis of the partial amino acid sequence, and the determination of the gene sequences of the 5'-end and the 3'-end using the 5' RACE method and 3' RACE method were performed. Consequently, it is concluded that the hemolytic active protein of *Carybdea rastonii* has the full primary amino acid sequence represented by (SEQ ID NO:5), and the gene encoding thereof has the base sequence represented by (SEQ ID NO:4).

The result of the homology search on these full primary amino acid sequences exhibited that the homology between the protein and the known proteins was low.

The method for preparing the specific protein of the present invention by separation and purification is characterized in retaining the hemolytic activity. For example, the separation and the purification in the state of retaining such hemolytic activity are attained by performing the processing such as ultrasonication using the above-mentioned phosphoric acid buffer solution or various high performance liquid chromatography in 10 mM phosphoric acid buffer solution (pH 6.0) containing above 0.1 M NaCl, preferably above 0.3 M, and more preferably above 0.5 M, at below 10° C., preferably below 5° C.

Therefore, the present invention also provides the method for preparing the protein by extracting and purifying them from the nematocyst of the *Carybdea rastonii* in the state of retaining the physiological activity.

The specific protein of the present invention also can be prepared by the gene recombination method. Preparation by the gene recombination method can be performed according to a conventional method. For example, it can be obtained by preparing the vector integrated with the gene represented by (SEQ ID NO:4), transforming a host cell by the vector, incubating or growing the host cell, and isolating and purifying the proteins having hemolytic activity of interest from the host cell or culture solution. Since the protein provided according to the present invention has a hemolytic activity, for example, it may be used for the medicaments having the platelet agglutination effect and for the reagents for research on a hemolysis. Furthermore, it provides the new approach for the development of drugs, such as a drug for treating the sting by the jellyfish, and development of pesticides, such as an insecticide, using the hemolytic activity.

EXAMPLES

The present invention will be described in detail with reference to the following examples; however, the present invention is not limited to the examples.

Example 1

1) Extraction of the Nematocyst of *Carybdea rastonii*

200 mg of the nematocyst of the *Carybdea rastonii* obtained on the Miura peninsula, Kanagawa, Japan and cryopreservated at −80° C. was immersed in 8 ml of 10 mM phosphoric acid buffer solution (pH 6.0), and treated for 15 minutes by the ultrasonic wave (ultrasonic cleaner VS150, Iuchi Co.). The supernatant fluids were collected by centrifugal separation (3,000 rpm, for 20 minutes). This operation was performed 3 times in total. Furthermore, the same extraction operation was repeated 3 times with 8 ml of 10 mM phosphoric acid buffer solutions (pH 6.0) containing 1 M NaCl, and then all the supernatant fluids were collected. After the extraction operation, ion exchange HPLC (high performance liquid chromatography) of the following purification step was immediately performed.

2) The Purification by Ion Exchange HPLC (Column: TSK-GEL CM650S, Column Size: 20×220 mm)

The above-mentioned column was equilibrated with 10 mM phosphoric acid buffer solution (pH 6.0) containing 0.3 M NaCl. After the equilibration, the supernatant fluids obtained by extraction in the operation of the above-mentioned 1) were combined and diluted with 10 mM phosphoric acid buffer solution (pH 6.0) to 4 times. The solution was loaded onto the above-mentioned column at a flow rate of the 3 ml/min. The column was washed with 100 ml of 10 mM phosphoric acid buffer solutions (pH 6.0) after the sample application. The elution was carried out by the 60 minutes gradient in 0 to 0.7 M NaCl concentration (in 10 mM phosphoric acid buffer solution: pH 6.0). Hemolytic activity was showed in many fractions eluting between 45 and 65 minutes after start of the gradient. In addition, hemolytic activity was examined about the hemolytic effect to sheep hemocytes (see the after-mentioned example 2).

3) The Purification by Ion Exchange HPLC (Column: TSK-GEL CM5PW, Column Size: 7.5×75 mm)

The above-mentioned column was well equilibrated with 10 mM phosphoric acid buffer solution (pH 6.0) containing 0.3 M NaCl. The hemolytic active fractions obtained by purifying operation of the above-mentioned 2) were diluted with 10 mM phosphoric acid buffer solution (pH 6.0) to 4 times. The solution was loaded onto the above-mentioned column at the flow rate of 2 ml/min. The column was washed with 30 ml of 10 mM phosphoric acid buffer solutions (pH 6.0) after the sample application. After washing, the elution was performed by the 60 min gradient in 0 to 0.8 M NaCl concentration (in 10 mM phosphoric acid buffer solution: pH 6.0). Fractions having hemolytic activity were eluted between 25 and 35 minutes after start of the gradient, and each fraction was applied to SDS-PAGE. The separating condition of the active component was verified, and the portions separated well were collected and used in the next step. On the contrary, the portions not separated were further performed by chromatography to complete the separation of the active component.

4) Concentration of the Hemolytic Active Component by Ion Exchange HPLC (Column: TSK-GEL CM5PW, Column Size: 7.5×75 mm)

The column was well equilibrated with 10 mM phosphoric acid buffer solution (pH 6.0) containing 0.3 M NaCl. The hemolytic active fractions obtained by purifying operation of above-mentioned 3) were diluted with 10 mM phosphoric acid buffer solution (pH 6.0) to 4 times. The solution was loaded onto the above-mentioned column at the flow rate of 2 ml/min. The column was washed with 30 ml of 10 mM phosphoric acid buffer solutions (pH 6.0) after the sample application. After washing, 10 mM phosphoric acid buffer solution (pH 6.0) containing 0.8 M NaCl was then rinsed and the sample adhered into the column was allowed to elute. In about 5 minutes after exchange of the solvent, the portion of the hemolytic active component condensed and eluted at a stretch was collected.

5) The Purification by Gel Filtration HPLC (Column: Superdex-75, Column Size: 16×600 mm)

Every 0.5-1.0 ml of the sample condensed by ion exchange HPLC was applied to the above-mentioned column equilibrated with 10 mM phosphoric acid buffer solution (pH 6.0) containing 0.8 M NaCl, and allowed to elute at the flow rate of 1 ml/min. Potent hemolytic activity was found out in the fraction eluting between 50 and 60 minutes after injection of the sample. After confirming the separating condition by SDS PAGE, the protein of the present invention, a hemolytic toxin, was separated by collecting the active fractions (about 1 μg).

Example 2

Measurement of the Hemolytic Activity

Measurement of the hemolytic activity in each purification step in the above-mentioned Example 1 and measurement of the hemolytic activity of the protein of the present invention finally obtained were performed as follows.

1) Method

Hemolytic activity was measured by hemolysis to a sheep erythrocyte. That is, every 200 μl of PBS(+) buffer solution containing 0.8% of sheep erythrocyte was put into the microwell plates of 96 wells (round bottom type). 10 μl of the solution dissolved the fraction obtained in each purification step of the above-mentioned Example 1 in 10 mM phosphoric acid buffer solution (pH 6.0) was added to the plate. It was allowed to stand at room temperature for 3 hours, and the hemolytic condition of the sheep erythrocyte of each plate was observed. In addition, the presence or absence of the retention of the hemolytic activity was determined by whether the fraction obtained in each purification step exhibits a perfect hemolysis.

2) Results 2-1) The fraction obtained in each purification step of the above-mentioned Example 1 exhibited the perfect hemolysis to the sheep erythrocyte, and therefore, it became clear that it retains the hemolytic activity.

2-2) Moreover, the protein of the present invention having the hemolytic activity finally obtained by purification operation of the above-mentioned 5) in Example 1 caused the perfect hemolysis to the sheep erythrocyte in the concentration below 100 ng/ml (about 2 nM).

Example 3

Determination of the Molecular Weight and the Partial Structure on the Proteins 3-1) Determination of the Molecular Weight The single band visualized by applying the protein of the present invention having the hemolytic activity obtained by purification operation of 5) in Example 1 to SDS gel electrophoresis (SDS-PAGE) according to the conventional method was compared with the protein molecular-weight marker (Pharmacia Co.). As the result, it was identified that the molecular weight of the protein of the present invention are about 50,000 Da.

3-2) Decomposition with the Lysylendopeptidase

The protein was decomposed by adding 3 pM of *Achromobacter* Protease I (derived from *Achromohacter lyticus* M497-1: Takara Shuzo Co.) to 10 μg of protein according to the present invention having the hemolytic activity obtained by purification operation of the above-mentioned 5) in Example 1, and incubating in 10 mM of Tris-HCl buffer solution (pH 9.0) at 30° C. for 20 hours. The protein digested with the enzyme was applied to the high performance liquid chromatography (column: Bakerbond wide pore ODS), and separated with the 60 min gradient in 10 to 62% of acetonitrile concentration (in water containing 0.1% of trifluoroacetic acid) at the flow rate of 0.7 ml/min. Consequently, three peptide fragments eluting respectively at a retention time 19, 23 and 27 minutes were obtained.

3-3) Determination of the Amino Acid Sequence of Each Fragments by the Amino Acid Sequencer The amino acid sequence of three peptide fragments obtained as mentioned above was determined according to the conventional method using Shimadzu PSQ-1 protein sequencer (Shimadzu Co.).

As the result, three fragments have the following amino acid sequences (1)-(3), respectively:

Amino acid sequence (1):

Gly-Glu-Ile-Gln-Thr-Lys-Pro-Asp-Arg- (SEQ ID NO: 1)
Val-Gly-Gln-Ala-Thr

Amino acid sequence (2):

Gly-Asn-Ala-Glu-His-Val-Ala-Ser-Ala- (SEQ ID NO: 2)
Val-Glu-Asn-Ala-Asn-Arg-Val-Asn-Lys

Amino acid sequence (3):

Met-Ser-Asp-Gly-Phe-Tyr-Thr-Met-Glu- (SEQ ID NO: 3)
Asn-Ser-Asp-Arg-Arg-Lys (wherein, an amino acid residue is written by the 3 letters notation defined by IUPAC and IUB).

The homology search about each fragment with which the amino acid sequence was determined as mentioned above exhibited that the homology between these fragments and the known proteins was very low. Therefore, it was suggested that the specific protein of the present invention fractionated from the nematocyst of *Carybdea rastonii* while retaining the hemolytic activity is completely novel protein.

Example 4

Determination of the Full Amino Acid Sequence of the Protein and the Gene Encoding the Amino Acids 4-1) Preparation of Total RNA of *Carybdea rastonii*

The tentacle (about 0.5 g in wet weights) of Carybdea rastonii was crushed in the liquid nitrogen, and homogenized in 5 ml TRIzol™ reagent (GIBCO BRL Co.). To this mixture was added 1 ml of chloroform, and the mixture was agitated, and centrifuged with the cooling centrifuge (Sakuma Co.) [13,000 rpm, for 15 minutes, at 4° C.]. The upper aqueous layer was fractionated, and to this solution was added 2.5 ml of isopropanol, then, the mixture was allowed to stand at room temperature for 10 minutes. The supernatant fluid was removed after the centrifugal separation (13,000 rpm, for 10 minutes, at 4° C.) using the cooling centrifuge, and then 5 ml of 75% ethanol was added the residue. The supernatant fluid was removed after the centrifuge (10,000 rpm, for 5 minutes, at 4° C.) to obtain the residue, then, the air-drying of the residue was performed for about 10 minutes. 100 μl of RNase-free water was added to the resulting residue, and the mixture was incubated for 10 minutes at 60° C. to lyse RNA. About 0.5 mg of total RNA was obtained according to the above-mentioned method.

4-2) Cloning of a Partial cDNA

On the basis of amino acid sequence (1), amino acid sequence (2) and amino acid sequence (3), the following degenerate primers were designed and synthesized by the conventional method:

```
7-F;    GAR ATH CAR ACI AAR CCI G    (SEQ ID NO: 6)
7-R;    CIG GYT TIG TYT GDA TYT C    (SEQ ID NO: 7)
```

-continued
```
12-F;   GCI GTI GAR AAY GCI AAY MG   (SEQ ID NO: 8)
12-R;   CKR TTI GCR TTY TCI ACI GC   (SEQ ID NO: 9)
14-1-F; GAY GGI TTY TAY ACI ATG G    (SEQ ID NO: 10)
14-1-R; CCA TIG TRT ARA AIC CRT C    (SEQ ID NO: 11)
12-2-F; GAY GGI TTY TAY ACI ATG      (SEQ ID NO: 12)
        GAR AA
12-2-R; TTY TCC ATI GTR TAR AAI      (SEQ ID NO: 13)
        CCR TC
```

(wherein, the above-mentioned alphabetic character was written based on the "Nucleotide Abbreviation List" (Cell Technology, separate volume, "*Biotechnology Experiment Illustrated*": Shujunsha Co.).

Next, according to the following procedure, single-strand cDNA was synthesized using SUPERSCRIPT™ Preamplification System for 1st-Strand cDNA Synthesis. That is, 1 μg of total RNA, oligo(dT)$_{12-18}$, and DEPC-treated water were mixed, and the mixture was allowed to stand for 10 minutes at 70° C. Then, PCR buffer, 25 mM MgCl$_2$, 10 mM dNTP mix, and 0.1 M DTT were added to this mixture, and the resulting mixture was pre-incubated for 5 minutes at 42° C. Superscript II RT (200 units/μl) was added to this mixture, and the mixture was incubated for 50 minutes at 42° C. and for 15 minutes at 70° C. The RNase H was added to the mixture, and then, the resulting mixture was incubated for 20 minutes at 37° C. to obtain 1st-strand cDNA.

Subsequently, according to the following conditions, PCR was performed using GeneAmp PCR System 2400 thermal cycler (Perkin-Elmer Co.). That is, 1st-strand cDNA, PCR buffer, dNTP mix, primer 1 and primer 2 (wherein, primer 1 and primer 2 are any eight above-mentioned primers.), TaKaRa Ex Taq™ (Takara Shuzo Co.), and water were mixed. The reaction was performed by heating the mixture at 94° C. for 5 minutes and repeating 3 cycles of 30 seconds at 94° C., 30 seconds at 45° C. and 2 minutes at 72° C., and 27 cycles of 30 seconds at 94° C., 30 seconds at 55° C. and 2 minutes at 72° C. The reactant was then treated for 5 minutes at 72° C.

The obtained reaction solution was electrophoresed on 0.8% agarose gel to confirm the amplified PCR products in the combination of 7-F and 12-R, 7-F and 14-1-R, 7-F and 14-2-R, 12-F and 14-1-R, and 12-F and 14-2-R. The sizes of each PCR product were about 600 bp, 1,000 bp, 1,000 bp, 400 bp, and 400 bp, respectively.

4-3) Sequencing of the Partial cDNA

Each PCR product was inserted into TA cloning vector pCR2.1 (Invitrogene Co.), and the recombinant was transformed to the *Escherichia coli* JM109. The transformant was cultured on LB (containing 50 μg/μl of ampicillin) agar medium. According to the following conditions, colony PCR was performed to the colonies obtained as a template using the M13 universal primer. The strain of *Escherichia coli*, PCR buffer, dNTP mix, M13 FW primer, M13 RV primer, TaKaRa Ex Taq™ (Takara Shuzo Co.), and water were mixed. The reaction was performed by heating the mixture at 90° C. for 10 minutes and repeating 30 cycles of 30 seconds at 94° C., 30 seconds at 55° C. and 2 minutes at 72° C., and then heating at 72° C. for 5 minutes. The reaction solution was electrophoresed on 0.8% agarose gel and the target colony PCR product was purified on the spin column of MicroSpin™ S-400 (Amersham Pharmacia Co.). Then, the sequencing of the obtained product was conducted by using ABI PRISM 310 Genetic Analyzer (Applied Biosystems Co.).

The obtained sequence was analyzed using gene analysis soft ware GENETYX-MAC (Software Development Co.). As the result, the partial cDNA sequence of about 1000 bp was analyzed, and each partial structure of amino acid sequence (1), amino acid sequence (2) and amino acid sequence (3) was determined to locate in this turn from N terminal of the protein.

4-4) Sequencing of the Full-Length cDNA

Following primers were synthesized based on the base sequence of the partial cDNA:

```
5'-RACE-4R;   GCT CTA TCA ATA ACG (SEQ ID NO: 14)
              GCA GC

5'-RACE-5R;   TGT CTT TGG ATG GCC (SEQ ID NO: 15)
              TCA TC

5'-RACE-6R;   GAT ACT TAG GTC GCT (SEQ ID NO: 16)
              ATC CG

3'-RACE-1F;   GTT CAG AGG CTG TTC (SEQ ID NO: 17)
              TAA CG

3'-RACE-2F;   ATG TCT GAC GGC TTC (SEQ ID NO: 18)
              TAC AC
```

Next, according to the following procedure, 5' RACE and 3' RACE were performed using 5'/3' RACE Kit (Boehringer Mannheim Co.).

(a) 5' RACE

1 µg of total RNA, cDNA synthesis buffer, dNTP mix, 5'-RACE-6R, AMV reverse transcriptase, and DEPC-treated water were mixed, and the mixture was incubated for 60 minutes at 55° C. and for 10 minutes at 65° C. to obtain 1st-strand cDNA.

Next, 1st-strand cDNA thus obtained was purified on the spin column, then, reaction buffer and 2 mM dATP were added to the 1st-strand cDNA, and the mixture was allowed to stand for 3 minutes at 94° C. Terminal transferase (10 units/µl) was added to the mixture, and the resulting mixture was incubated for 20 minutes at 37° C. After the incubation, 1st-strand cDNA, PCR buffer, dNTP mix, 5'-RACE-5R, oligo(dT)-anchor primer, and water were added to the above mixture. The reaction was performed by heating the mixture at 94° C. for 5 minutes and repeating 30 cycles of 30 seconds at 94° C., 30 seconds at 55° C. and 1 minute at 72° C., and then heating at 72° C. for 5 minutes. Consequently, the nested-PCR was performed to the 1st-PCR product as a template using the combination of 5'-RACE-4R and PCR anchor primer under the same condition as 1st-PCR.

The 1st-PCR product and the nested-PCR product were electrophoresed on 1.5% agarose gel to confirm the band of about 500 bp. This nested-PCR product was inserted into TA cloning vector, and the sequencing was performed according to the determination of the base sequence of cDNA described in the above-mentioned 4-3), then the sequence was analyzed.

(b) 3' RACE

1 µg of total RNA, cDNA synthesis buffer, dNTP mix, oligo(dT)-anchor primer, AMV reverse transcriptase, and DEPC-treated water were mixed, and the mixture was incubated for 60 minutes at 55° C. Subsequently, the reactant was treated for 10 minutes at 65° C. to obtain 1st-strand cDNA.

Next, 1st-PCR thus obtained was performed under the following condition. 1st-strand cDNA, PCR buffer, dNTP mix, 3'-RACE-1F, PCR anchor primer, TaKaRa Ex Taq™ (Takara Shuzo Co.), and water were mixed. The reaction was performed by heating the mixture at 94° C. for 5 minutes and repeating 30 cycles of 30 seconds at 94° C., 30 seconds at 55° C. and 2 minutes at 72° C., and then heating at 72° C. for 5 minutes. The nested-PCR was performed to the 1st-PCR product as a template using the combination of 3'-RACE-2F and PCR anchor primer under the same condition as 1st-PCR.

The 1st-PCR product and the nested-PCR product were electrophoresed on 1.5% agarose gel to confirm the band of about 600 bp. The nested-PCR product was inserted into TA cloning vector, the sequencing was performed according to the determination of the base sequence of cDNA described in the above-mentioned 4-3), and the sequence was analyzed.

As a result, the size (1610 bp) and the sequence of cDNA encoding the novel hemolytic active protein of Carybdea rastonii, and the number (450aa) and the sequence of amino acid of the protein became clear. That is, the hemolytic active protein of Carybdea rastonii had the amino acid sequence represented by (SEQ ID NO:5), and the gene encoding thereof had the base sequence represented by (SEQ ID NO:4).

The amino acid sequence (1) (SEQ ID NO:1), the amino acid sequence (2) (SEQ ID NO:2), and the amino acid sequence (3) (SEQ ID NO:3) corresponded to the amino acid number 56-69 of (SEQ ID NO:5), the amino acid number 250-267 of (SEQ ID NO:5), and the amino acid number 363-377 of (SEQ ID NO:5), respectively. Furthermore, it was confirmed that the poly A sequence exists after the nucleotide number 1600 of (SEQ ID NO:4).

The novel protein of the present invention obtained as mentioned above is the specific protein having the following physiological activity, and physical and chemical property, as indicated by the example:

(a) having hemolytic activity;

(b) having a molecular weight of about 50,000 Da (determined by SDS gel electrophoresis);

(c) having the amino acid sequences 1 to 3 described above as a partial amino acid sequence; and (d) having the amino acid sequence represented by SEQ ID NO 5 as the full amino acid sequence.

INDUSTRIAL APPLICABILITY

Since the protein having the hemolytic activity derived from the nematocyst of *Carybdea rastonii* provided according to the present invention is a novel protein which is not similar to known protein, as a result of the homology search on the partial amino acid sequence and the full primary amino acid sequences, it is useful as a biochemical reagent for example, elucidating the mechanism of a hemolysis etc.

It also provides the new approach directed to development of drugs, such as the medicine for treating the sting by the jellyfish, on the basis of study of correlation of the structural activity in a molecular level, and the antibody on the protein or the partial peptide, etc. Furthermore, it is useful as the drugs having a platelet agglutination effect etc., and pesticides using a hemolytic activity.

What is claimed is:

1. An isolated antibody specifically reactive with a protein which consists of the amino acid residue sequence of SEQ ID NO:1, SEQ ID NO:2, SEQ ID NO:3, or SEQ ID NO:5, wherein said protein has hemolytic activity.

2. A composition comprising the antibody according to claim 1.

* * * * *

SEQUENCE LISTING

<160> NUMBER OF SEQ ID NOS: 5

<210> SEQ ID NO 1
<211> LENGTH: 14
<212> TYPE: PRT
<213> ORGANISM: CARYBDEA RASTONII
<220> FEATURE:
<221> NAME/KEY: PEPTIDE
<222> LOCATION: (1)..(14)

<400> SEQUENCE: 1

Gly Glu Ile Gln Thr Lys Pro Asp Arg Val Gly Gln Ala Thr
 1               5                  10

<210> SEQ ID NO 2
<211> LENGTH: 18
<212> TYPE: PRT
<213> ORGANISM: CARYBDEA RASTONII
<220> FEATURE:
<221> NAME/KEY: PEPTIDE
<222> LOCATION: (1)..(18)

<400> SEQUENCE: 2

Gly Asn Ala Glu His Val Ala Ser Ala Val Glu Asn Ala Asn Arg Val
 1               5                  10                  15

Asn Lys

<210> SEQ ID NO 3
<211> LENGTH: 15
<212> TYPE: PRT
<213> ORGANISM: CARYBDEA RASTONII

<400> SEQUENCE: 3

Met Ser Asp Gly Phe Tyr Thr Met Glu Asn Ser Asp Arg Arg Lys
 1               5                  10                  15

<210> SEQ ID NO 4
<211> LENGTH: 1610
<212> TYPE: DNA
<213> ORGANISM: CARYBDEA RASTONII
<220> FEATURE:
<221> NAME/KEY: protein_bind
<222> LOCATION: (1)..(27)
<220> FEATURE:
<221> NAME/KEY: CDS
<222> LOCATION: (28)..(1380)
<220> FEATURE:
<221> NAME/KEY: protein_bind
<222> LOCATION: (1381)..(1610)

<400> SEQUENCE: 4

```
gcacaagcga cttggtgaag gagcacc atg att ctg aaa cat ctt cct tgg ctc      54
                            Met Ile Leu Lys His Leu Pro Trp Leu
                              1               5 ttt att gtc ctt gca att act tct gca aaa cat ggc aaa cgc tct gat       102
Phe Ile Val Leu Ala Ile Thr Ser Ala Lys His Gly Lys Arg Ser Asp
 10              15                  20                  25 gtc aat tct tta ctt act aag gta gaa act gcc tta aaa gaa gct tct       150
Val Asn Ser Leu Leu Thr Lys Val Glu Thr Ala Leu Lys Glu Ala Ser
                 30                  35                  40 ggt agc aac gag gct gct ctt gag gct tta gag ggc tta aaa gga gag       198
Gly Ser Asn Glu Ala Ala Leu Glu Ala Leu Glu Gly Leu Lys Gly Glu
             45                  50                  55 atc cag aca aaa cca gac cga gtt gga caa gcc aca aaa atc ctt gga       246
```

```
                Ile Gln Thr Lys Pro Asp Arg Val Gly Gln Ala Thr Lys Ile Leu Gly
                             60                  65                  70 tct gtc gga tca gct cta gga aaa tta aat tct gga gat gca acc aaa                294
Ser Val Gly Ser Ala Leu Gly Lys Leu Asn Ser Gly Asp Ala Thr Lys
         75                  80                  85 atc att tct ggt tgc ctc gac att gtt gca gga att gca aca act ttt                342
Ile Ile Ser Gly Cys Leu Asp Ile Val Ala Gly Ile Ala Thr Thr Phe
 90                  95                 100                 105 gga ggc cct gtc ggg atg gga atc gga gcc gta gct tct ttt gtt tct                390
Gly Gly Pro Val Gly Met Gly Ile Gly Ala Val Ala Ser Phe Val Ser
                    110                 115                 120 tca att cta tca ttg ttt act gga agc tca gca aag aac tca gtt gct                438
Ser Ile Leu Ser Leu Phe Thr Gly Ser Ser Ala Lys Asn Ser Val Ala
            125                 130                 135 gcc gtt att gat aga gct tta agc aag cat cgc gat gag gcc atc caa                486
Ala Val Ile Asp Arg Ala Leu Ser Lys His Arg Asp Glu Ala Ile Gln
        140                 145                 150 aga cat gca gca ggt gcc aag aga gat ttt gct gaa tca tct gca ttc                534
Arg His Ala Ala Gly Ala Lys Arg Asp Phe Ala Glu Ser Ser Ala Phe
    155                 160                 165 att cag gtc atg aaa cag cag tcc aat ctt aca gat agc gac cta agt                582
Ile Gln Val Met Lys Gln Gln Ser Asn Leu Thr Asp Ser Asp Leu Ser
170                 175                 180                 185 atc att gca gcg aat gtt cct gtt tat aaa ttt agt aat ttt atc gga                630
Ile Ile Ala Ala Asn Val Pro Val Tyr Lys Phe Ser Asn Phe Ile Gly
                190                 195                 200 cag ttg gag agc aga att tcc caa ggc gca gca act acc agt ctt agc                678
Gln Leu Glu Ser Arg Ile Ser Gln Gly Ala Ala Thr Thr Ser Leu Ser
            205                 210                 215 gat gca aag aga gcc gtt gac ttc att ctg ctc tat tgt caa ctt gta                726
Asp Ala Lys Arg Ala Val Asp Phe Ile Leu Leu Tyr Cys Gln Leu Val
        220                 225                 230 gtc atg aga gaa acc ttg ctg gtc gac ttg gct att ctc tac agg aaa                774
Val Met Arg Glu Thr Leu Leu Val Asp Leu Ala Ile Leu Tyr Arg Lys
    235                 240                 245 gga aat gca gaa cac gtg gca agt gct gtg gaa aac gct aat agg gta                822
Gly Asn Ala Glu His Val Ala Ser Ala Val Glu Asn Ala Asn Arg Val
250                 255                 260                 265 aac aaa gag cta gct gct gat acc cta gat ttt ctt cat aaa ttg att                870
Asn Lys Glu Leu Ala Ala Asp Thr Leu Asp Phe Leu His Lys Leu Ile
                270                 275                 280 cct gaa caa gca ttg ata ggt gca gtt tat cat cca att tct gcc tct                918
Pro Glu Gln Ala Leu Ile Gly Ala Val Tyr His Pro Ile Ser Ala Ser
            285                 290                 295 gaa act agc aaa gca ata tta aat tac acg aaa tac ttt gga gtt cca                966
Glu Thr Ser Lys Ala Ile Leu Asn Tyr Thr Lys Tyr Phe Gly Val Pro
        300                 305                 310 gat gtt ccc cgt cct att gga aac cgc aga tac aaa ttt aca aat agt               1014
Asp Val Pro Arg Pro Ile Gly Asn Arg Arg Tyr Lys Phe Thr Asn Ser
    315                 320                 325 tac tgg aat acc tac agt ata tgc agt gag gct tac atg gga aat tac               1062
Tyr Trp Asn Thr Tyr Ser Ile Cys Ser Glu Ala Tyr Met Gly Asn Tyr
330                 335                 340                 345 atg ttc aga ggc tgt tct aac gtt cgg aat cca aat atc agg gta tcc               1110
Met Phe Arg Gly Cys Ser Asn Val Arg Asn Pro Asn Ile Arg Val Ser
                350                 355                 360 aaa atg tct gat ggg ttt tac acc atg gag aat agc gat cgg agg aag               1158
Lys Met Ser Asp Gly Phe Tyr Thr Met Glu Asn Ser Asp Arg Arg Lys
            365                 370                 375
```

```
ttg tat atc acc aag cat gac caa gga tgg gga tgg ggt act ttg gat    1206
Leu Tyr Ile Thr Lys His Asp Gln Gly Trp Gly Trp Gly Thr Leu Asp
        380                 385                 390 gag gat cca ggt gac caa ggc cat atg agg ttc att cct ttg aga cat    1254
Glu Asp Pro Gly Asp Gln Gly His Met Arg Phe Ile Pro Leu Arg His
    395                 400                 405 ggg aag tat atg gta agc tct aag agg tgg ccc aac tgg ttc atg tat    1302
Gly Lys Tyr Met Val Ser Ser Lys Arg Trp Pro Asn Trp Phe Met Tyr
410                 415                 420                 425 atg gaa tca agt gcc agt ggc tac att cgc agc tgg gaa aat aat cca    1350
Met Glu Ser Ser Ala Ser Gly Tyr Ile Arg Ser Trp Glu Asn Asn Pro
                430                 435                 440 gga cct caa gga cat tgg agt ata aca taa ttaaagagga atcaacaatg      1400
Gly Pro Gln Gly His Trp Ser Ile Thr
            445                 450 tcccaaggc atacgaatat aagacatcaa acgaatgcag tacttaaagt gcacacttgt   1460
atttctacat aggatgtcgt catgaaagtc cataaaccat ccagcggact aatttctat   1520 taaacattaa tgtttcctta taatgcattt tcatgaaatc tctattgtga catttcaaga  1580
ggatatgttt gaaagaaaca aaaaaaaaaa                                   1610

<210> SEQ ID NO 5
<211> LENGTH: 450
<212> TYPE: PRT
<213> ORGANISM: CARYBDEA RASTONII

<400> SEQUENCE: 5

Met Ile Leu Lys His Leu Pro Trp Leu Phe Ile Val Leu Ala Ile Thr
 1               5                  10                  15

Ser Ala Lys His Gly Lys Arg Ser Asp Val Asn Ser Leu Leu Thr Lys
            20                  25                  30

Val Glu Thr Ala Leu Lys Glu Ala Ser Gly Ser Asn Glu Ala Ala Leu
        35                  40                  45

Glu Ala Leu Glu Gly Leu Lys Gly Glu Ile Gln Thr Lys Pro Asp Arg
    50                  55                  60

Val Gly Gln Ala Thr Lys Ile Leu Gly Ser Val Gly Ser Ala Leu Gly
65                  70                  75                  80

Lys Leu Asn Ser Gly Asp Ala Thr Lys Ile Ile Ser Gly Cys Leu Asp
                85                  90                  95

Ile Val Ala Gly Ile Ala Thr Thr Phe Gly Gly Pro Val Gly Met Gly
            100                 105                 110

Ile Gly Ala Val Ala Ser Phe Val Ser Ser Ile Leu Ser Leu Phe Thr
        115                 120                 125

Gly Ser Ser Ala Lys Asn Ser Val Ala Ala Val Ile Asp Arg Ala Leu
    130                 135                 140

Ser Lys His Arg Asp Glu Ala Ile Gln Arg His Ala Ala Gly Ala Lys
145                 150                 155                 160

Arg Asp Phe Ala Glu Ser Ser Ala Phe Ile Gln Val Met Lys Gln Gln
                165                 170                 175

Ser Asn Leu Thr Asp Ser Asp Leu Ser Ile Ile Ala Ala Asn Val Pro
            180                 185                 190

Val Tyr Lys Phe Ser Asn Phe Ile Gly Gln Leu Glu Ser Arg Ile Ser
        195                 200                 205

Gln Gly Ala Ala Thr Thr Ser Leu Ser Asp Ala Lys Arg Ala Val Asp
    210                 215                 220

Phe Ile Leu Leu Tyr Cys Gln Leu Val Val Met Arg Glu Thr Leu Leu
```

-continued

```
225                 230                 235                 240
Val Asp Leu Ala Ile Leu Tyr Arg Lys Gly Asn Ala Glu His Val Ala
            245                 250                 255

Ser Ala Val Glu Asn Ala Asn Arg Val Asn Lys Glu Leu Ala Ala Asp
            260                 265                 270

Thr Leu Asp Phe Leu His Lys Leu Ile Pro Glu Gln Ala Leu Ile Gly
            275                 280                 285

Ala Val Tyr His Pro Ile Ser Ala Ser Glu Thr Ser Lys Ala Ile Leu
            290                 295                 300

Asn Tyr Thr Lys Tyr Phe Gly Val Pro Asp Val Pro Arg Pro Ile Gly
305                 310                 315                 320

Asn Arg Arg Tyr Lys Phe Thr Asn Ser Tyr Trp Asn Thr Tyr Ser Ile
            325                 330                 335

Cys Ser Glu Ala Tyr Met Gly Asn Tyr Met Phe Arg Gly Cys Ser Asn
            340                 345                 350

Val Arg Asn Pro Asn Ile Arg Val Ser Lys Met Ser Asp Gly Phe Tyr
            355                 360                 365

Thr Met Glu Asn Ser Asp Arg Arg Lys Leu Tyr Ile Thr Lys His Asp
            370                 375                 380

Gln Gly Trp Gly Trp Gly Thr Leu Asp Glu Asp Pro Gly Asp Gln Gly
385                 390                 395                 400

His Met Arg Phe Ile Pro Leu Arg His Gly Lys Tyr Met Val Ser Ser
            405                 410                 415

Lys Arg Trp Pro Asn Trp Phe Met Tyr Met Glu Ser Ser Ala Ser Gly
            420                 425                 430

Tyr Ile Arg Ser Trp Glu Asn Asn Pro Gly Pro Gln Gly His Trp Ser
            435                 440                 445

Ile Thr
450
```